United States Patent
Suri et al.

(10) Patent No.: US 9,624,277 B2
(45) Date of Patent: Apr. 18, 2017

(54) ANTICANCER AGENT

(75) Inventors: Anil Suri, New Delhi (IN); Deepika Kanojia, New Delhi (IN); Prabhakar Salunkhe, Dist-Jalgaon (IN); Sidharth Mahali, Orissa (IN); Sunil Kumar Manna, District-Midnapur East (IN); Avadhesha Surolia, New Delhi (IN); Ananda Chakrabarty, Villa Park, IL (US)

(73) Assignee: AMRITA THERAPEUTICS LIMITED, Ahmedabad (IN)

( * ) Notice: Subject to any disclaimer, the term of this patent is extended or adjusted under 35 U.S.C. 154(b) by 18 days.

(21) Appl. No.: 13/877,304

(22) PCT Filed: Sep. 30, 2011

(86) PCT No.: PCT/IN2011/000680
§ 371 (c)(1),
(2), (4) Date: Oct. 30, 2013

(87) PCT Pub. No.: WO2012/042540
PCT Pub. Date: Apr. 5, 2012

(65) Prior Publication Data
US 2014/0051643 A1    Feb. 20, 2014

(30) Foreign Application Priority Data
Oct. 1, 2010  (IN) .......................... 2754/MUM/2010

(51) Int. Cl.
C07K 14/45   (2006.01)
C07K 14/35   (2006.01)
A61K 38/16   (2006.01)

(52) U.S. Cl.
CPC ............ C07K 14/45 (2013.01); A61K 38/164 (2013.01); C07K 14/35 (2013.01)

(58) Field of Classification Search
None
See application file for complete search history.

(56) References Cited

U.S. PATENT DOCUMENTS 6,596,281 B1 *  7/2003  Gennaro ................ C07K 14/35
                                                    424/184.1
2008/0199493 A1 *  8/2008  Picker et al. ............. 424/208.1

OTHER PUBLICATIONS

UniProt sequence B2ZSG8 (Integrated into UniProt Jul. 1, 2008).*
Bailon et al. ("PEG-modified biopharmaceuticals"; Expert Opinion Drug Delivery (2009) 6(1)).*
Ananda M. Chakrabarty, "Bioengineered bugs, drugs and contentious issues in patenting", Bioengineered Bugs, vol. 1, Issue 1, p. 2-8; Jan./Feb. 2010.
Chaudhari et al., "Cupredoxin-cancer interrelationship: azurin binding with EphB2, interference in ephb2 tyrosine phosphorylation, and inhibition of cancer growth", Biochemistry vol. 46, No. 7, 1799-1810, Jan. 24, 2007.
Fialho et al., "Promiscuous anticancer drugs from pathogenic bacteria: rational versus intelligent drug design", Emerging Cancer Therapy: Microbial Approaches and Biotechnological Tools, eds. Arsenio M. Fialho and Ananda M. Chakrabarty, John Wiley & Sons, 2010.
Goselink et al., "Colony growth of human hematopoietic progenitor cells in the absence of serum is supported by a proteinase inhibitor identified as antileukoproteinase", J. Exp. Med. vol. 184, p. 1305-1312, Oct. 1996.
Hong et al., "Disrupting the entry barrier and attacking brain tumors", Cell Cycle 5:15, 1633-1641, Aug. 1, 2006.
Jemal et al., "Cancer statistics, 2008", CA Cancer J Clin 2008;58:71-96, Mar./Apr. 2008.
Kanojia et al., "Sperm-associated antigen 9 is a novel biomarker for colorectal cancer and is involved in tumor growth and tumorigenicity", Am. Jur. Pathology vol. 178, No. 3, Mar. 2011.
Ludwig et al., "Tumor necrosis factor-related apoptosis-inducing ligand: a novel mechanism for bacillus calmette-guérin-induced antitumor activity", Cancer Res. 64, 3386-3390, May 15, 2004.

* cited by examiner

Primary Examiner — James H Alstrum Acevedo
Assistant Examiner — Tara Martinez
(74) Attorney, Agent, or Firm — Lin Sun-Hoffman

(57) ABSTRACT

The present invention thus provides microbial products as anticancer agents and pharmaceutical compositions comprising isolated and purified proteins or synthetic peptides, and methods of using them for the treatment of cancer. It is very important to develop new anticancer bioactive peptides having high activity and low toxicity; given that most currently available anticancer therapies either have significant toxicity, and/or are prone to development of resistance.

2 Claims, 7 Drawing Sheets

SEQUENCE LISTING

<160> NUMBER OF SEQ ID NOS: 5

<210> SEQ ID NO 1
<211> LENGTH: 159
<212> TYPE: PRT
<213> ORGANISM: Mycobacterium bovis

<400> SEQUENCE: 1

Met Lys Leu Thr Thr Met Ile Lys Thr Ala Val Ala Val Val Ala Met
1               5                   10                  15

Ala Ala Ile Ala Thr Phe Ala Glu Pro Val Ala Leu Ala Ala Tyr Pro
            20                  25                  30

Ile Thr Gly Lys Leu Gly Ser Glu Leu Thr Met Thr Asp Thr Val Gly
        35                  40                  45

Gln Val Val Leu Gly Trp Lys Val Ser Asp Leu Lys Ser Ser Thr Ala
    50                  55                  60

Val Ile Pro Gly Tyr Pro Val Ala Gly Gln Val Trp Glu Ala Thr Ala
65                  70                  75                  80

Thr Val Asn Ala Ile Arg Gly Ser Val Thr Pro Ala Val Ser Gln Phe
                85                  90                  95

Asn Ala Arg Thr Ala Asp Gly Ile Asn Tyr Arg Val Leu Trp Gln Ala
            100                 105                 110

Ala Gly Pro Asp Thr Ile Ser Gly Ala Thr Ile Pro Gln Gly Glu Gln
        115                 120                 125

Ser Thr Gly Lys Ile Tyr Phe Asp Val Thr Gly Pro Ser Pro Thr Ile
    130                 135                 140

Val Ala Met Asn Asn Gly Met Gln Asp Leu Leu Ile Trp Glu Pro
145                 150                 155

<210> SEQ ID NO 2
<211> LENGTH: 319
<212> TYPE: PRT
<213> ORGANISM: Toxoplasma gondii

<400> SEQUENCE: 2

Met Phe Pro Lys Ala Val Arg Arg Ala Val Thr Ala Gly Val Phe Ala
1               5                   10                  15

Ala Pro Thr Leu Met Ser Phe Leu Arg Cys Gly Val Met Ala Ser Asp
            20                  25                  30

Pro Pro Leu Val Ala Asn Gln Val Val Thr Cys Pro Asp Lys Lys Ser
        35                  40                  45

Thr Ala Ala Val Ile Leu Thr Pro Thr Glu Asn His Phe Thr Leu Lys
    50                  55                  60

Cys Pro Lys Thr Ala Leu Thr Glu Pro Thr Leu Ala Tyr Ser Pro
65                  70                  75                  80

Asn Arg Gln Ile Cys Ser Ala Gly Thr Thr Ser Ser Cys Thr Ser Lys
                85                  90                  95

Ala Val Thr Leu Ser Ser Leu Ile Pro Glu Ala Glu Asp Ser Trp Trp
            100                 105                 110

Thr Gly Asp Ser Ala Ser Leu Asp Thr Ala Gly Ile Lys Leu Thr Val
        115                 120                 125

Pro Ile Glu Lys Phe Pro Val Thr Gln Thr Phe Val Val Gly Cys
    130                 135                 140

Ile Lys Gly Asp Asp Ala Gln Ser Cys Met Val Thr Val Thr Val Gln
145                 150                 155                 160

Ala Arg Ala Ser Ser Val Val Asn Asn Val Ala Arg Cys Ser Tyr Gly

-continued

```
                165                 170                 175

Ala Asn Ser Thr Leu Gly Pro Val Lys Leu Ser Ala Glu Gly Pro Thr
            180                 185                 190

Thr Met Thr Leu Val Cys Gly Lys Asp Gly Val Lys Val Pro Gln Asp
        195                 200                 205

Asn Asn Gln Tyr Cys Ser Gly Thr Thr Leu Thr Gly Cys Asn Glu Lys
    210                 215                 220

Ser Phe Lys Asp Ile Leu Pro Lys Leu Thr Glu Asn Pro Trp Gln Gly
225                 230                 235                 240

Asn Ala Ser Ser Asp Lys Gly Ala Thr Leu Thr Ile Lys Lys Glu Ala
                245                 250                 255

Phe Pro Ala Glu Ser Lys Ser Val Ile Ile Gly Cys Thr Gly Gly Ser
            260                 265                 270

Pro Glu Lys His His Cys Thr Val Lys Leu Glu Phe Ala Gly Ala Ala
        275                 280                 285

Gly Pro Ala Lys Ser Ala Ala Gly Thr Ala Ser His Val Ser Ile Phe
    290                 295                 300

Ala Met Val Ile Gly Leu Ile Gly Ser Phe Ala Ala Cys Val Ala
305                 310                 315

<210> SEQ ID NO 3
<211> LENGTH: 30
<212> TYPE: PRT
<213> ORGANISM: Mycobacterium bovis

<400> SEQUENCE: 3

Gly Gln Val Trp Glu Ala Thr Ala Thr Val Asn Ala Ile Arg Gly Ser
1               5                   10                  15

Val Thr Pro Ala Val Ser Gln Phe Asn Ala Arg Thr Ala Asp
            20                  25                  30

<210> SEQ ID NO 4
<211> LENGTH: 20
<212> TYPE: PRT
<213> ORGANISM: Toxoplasma gondii

<400> SEQUENCE: 4

Asn His Phe Thr Leu Lys Cys Pro Lys Thr Ala Leu Thr Glu Pro Pro
1               5                   10                  15

Thr Leu Ala Tyr
            20

<210> SEQ ID NO 5
<211> LENGTH: 23
<212> TYPE: PRT
<213> ORGANISM: Toxoplasma gondii

<400> SEQUENCE: 5

Thr Ala Gly Ile Lys Leu Thr Val Pro Ile Glu Lys Phe Pro Val Thr
1               5                   10                  15

Thr Gln Thr Phe Val Val Gly
            20
```

ANTICANCER AGENT

This application is a the U.S. National Phase Application of PCT/IN2011/000680, flied Sep. 30, 2011, which claims priority to Indian Patent Application No. 2754/MUM/2010, filed Oct. 1, 2010, the contents of such applications being Incorporated by reference herein.

FIELD OF THE INVENTION

The present invention particularly relates to a broad spectrum anticancer agent that is of microbial origin. More particularly, the invention relates to proteins either secreted by or surface associated in microorganisms including but not limiting to bacteria both pathogenic and nonpathogenic, viruses, and/or parasites. The anticancer agents of the present invention are purified proteins isolated from bacteria and parasites. Specifically, the agent of the present invention comprising at least proteins isolated from *Mycobacterium bovis* BCG, and *Toxoplasma gondii*. It also encompasses peptides derived from such proteins, synthetically prepared peptides, and proteins or peptides modified by PEGylation, acetylation, phosphorylation, etc. The proteins or various truncated derivatives thereof possess enhanced efficacy and reduced toxicity. The modifications made to the active purified proteins and peptides extend half life of the active ingredient or reduce immunogenecity in the patient blood stream.

The present invention also discloses the compositions, pharmaceutical compositions and the manner of its applications as therapeutic agent to treat mammalian cancer. The pharmaceutical composition comprises an active ingredient i.e. proteins, peptides, including PEGylated, acetylated, phosphorylated form thereof in isolation or in combination and physiologically and pharmaceutically accepted adjuvants or excipients.

BACKGROUND OF THE INVENTION

Bladder cancer is one of the deadliest forms of cancer, considered the sixth most common cause of cancer-related death in the United States (Jemal et al., 2008). One of the major weapons in the arsenal of cancer fighting drugs is the use of the bacterium *Mycobacterium bovis* (*Bacillus Calmette-Guerin*, BCG) since 1976 to fight superficial urothelial carcinoma of the bladder (Herr and Morales, 2008; Kresowik and Griffith, 2010). For its use as an anticancer therapy, live BCG cells are taken from lyophilized powders and introduced into emptied bladders through a urethral catheter. After a residence varying from a few minutes to a few hours, the BCG cells are eliminated by the patients through emptying of the bladder. The patients are subsequently monitored by cystoscopy, conventional cytology and FISH analysis. The BCG effect is believed to be mediated through induction of an immune reaction in the bladder such as release of cytokines IL 8 and TRAIL that leads to tumoricidal activity (Herr and Morales, 2008; Kresowik and Griffith, 2010). This immune response is greatly amplified with repeated instillations of BCG, demonstrating the importance of elevated cytokine levels including IL2, IL6, IL8, TNF, and IFNs (Shintani et al., 2007; Bisiaux et al., 2009) and the subsequent infiltrations of neutrophils, lymphocytes, and monocytes/macrophages. Indeed, BCG-stimulated neutrophils have been shown to kill bladder cancer cells in vitro in a TRAIL-dependent manner (Ludwig et al., 2004).

Unfortunately, therapeutic use of live BCG cells for bladder cancer treatment is associated with many debilitating and/or serious side effects, ranging from cystitis and gross hematuria to life-threatening BCG sepsis. Such major side effects during intravesical BCG therapy can affect treatments in 30% of patients while mild cystitis, malaise, low grade fever and other side effects are common in about 90% of patients (Bohle et al., 2003; Sylvester et al., 2003).

Further, some recent observations endorses that certain single nucleotide polymorphisms (SNPs) in humans can promote disease progression in spite of BCG therapy (Basturk et al., 2006; Decobert et al., 2006), making use of the immune response-invoking live BCG bacteria less effective in such patients. Thus toxicity and efficacy issues have been a major deterrent in the use of live BCG cells in bladder cancer immunotherapy.

The ability of *M. bovis* BCG to attack cancer cells and suppress their growth is not unique to this organism. Indeed, many other bacteria such as *Salmonella, Clostridia, Listeria*, etc, are known to allow cancer regression both by inducing an immune response as well as actively growing in the core of the tumor (Mahfouz et al., 2007; Fialho and Chakrabarty, 2010a). Even many viruses have been designed for cancer therapy (Fialho and Chakrabarty, 2010a). Recently pathogenic bacteria such as *Pseudomonas aeruginosa* or *gonococci/meningococci* such as *Neisseria meningitides* reported to produce proteins such as azurin or Laz that demonstrate strong anticancer activity both in vivo and in vitro (Chakrabarty, 2010; Fialho and Chakrabarty 2010 a,b). Not only the full-length proteins, but peptides derived from them such as the 28 amino acid peptide P28 or the 26 amino acid peptide P26, derived from different parts of azurin, show entry specificity in cancer cells (Taylor et al., 2009) and high cytotoxicity in cancers such as breast, melanoma, prostate, brain, etc (Taylor et al., 2009, Chaudhari et al., 2007). Proteins such as azurin, considered a bacterial weapon against cancer (Chakrabarty, 2010; Fialho and Chakrabarty, 2010b), are secreted in response to the presence of cancer cells (Mahfouz et al., 2007), while the *Neisserial* protein weapon Laz is surface-exposed (Hong et al., 2006). The phase I human clinical trials of p28 were performed as per US-FDA guidelines. The p28 peptide has shown lack of toxicity and partial tumor regression in 2 patients and complete regression in 2 other patients out of 15 advanced stage (stage IV) cancer patients where no drugs were working and where the patients had less than 6 months life span. When given in 5 escalating doses 3 times a week for 4 weeks, followed by a break of 2 weeks, several patients showed stunted tumor growth but 2 patients showed partial regression and 2 patients showed complete regression of their tumors (where no drugs were working any longer). The 2 patients where the tumors completely regressed (making them disease free) as well as another patient (altogether 3) are alive today (middle of August 2011) beyond one and a half year (Richards et al., 2011), showing that such bacterial peptides as p28, derived from azurin, have unique modes of action so that they work against drug-resistant cancers. We hope that the newly identified peptide MB30 will behave similarly.

To the best of the knowledge of the applicant and/or inventors, no efforts have been made to look for protein/peptide weapons produced by such bacteria. However, considering the ability of microbial products being used as potential anticancer agent, the applicant/inventors carried out pains taking research to arrive at other protein weapons, either secreted or surface-associated in microorganisms including pathogens, or that could be designed as synthetic peptides, that would demonstrate anticancer activity for use as anticancer therapies instead of the live bacteria.

OBJECT OF THE INVENTION

The main object is to provide an anticancer agent pharmaceutical compositions and application thereof eliminating the limitations of prior art.

The other object is to provide an anticancer agent, particularly broad spectrum anticancer agent of microbial origin, more particularly, proteins either secreted by or surface associated in microorganisms including but not limiting to bacteria both pathogenic and nonpathogenic, viruses, and/or parasites.

Yet another object is to provide purified proteins isolated from bacteria and parasites specifically, proteins isolated from M. bovis BCG, and Toxoplasma gondii useful as an anticancer agent.

Still other object is to provide peptides derived from such proteins, synthetically prepared peptides, and proteins or peptides modified by PEGylation, acetylation, phosphorylation, etc. useful as an anticancer agent.

Still another object is to also provide anticancer agent comprising the proteins or various truncated derivatives thereof that possess enhanced efficacy and reduced toxicity.

Yet other object is to provide purified proteins and peptides, as an anticancer agent, with extended half life and reduced immunogeoicity in the patient blood stream.

The other object of the present invention also discloses the compositions, pharmaceutical compositions and the manner of its applications as therapeutic agent to treat mammalian cancer.

The pharmaceutical composition comprises an active ingredient i.e. proteins, peptides, including PEGylated, acetylated, phosphorylated form thereof in isolation or in combination and physiologically and pharmaceutically accepted adjuvants or excipients.

SUMMARY OF THE INVENTION

Figure 1:
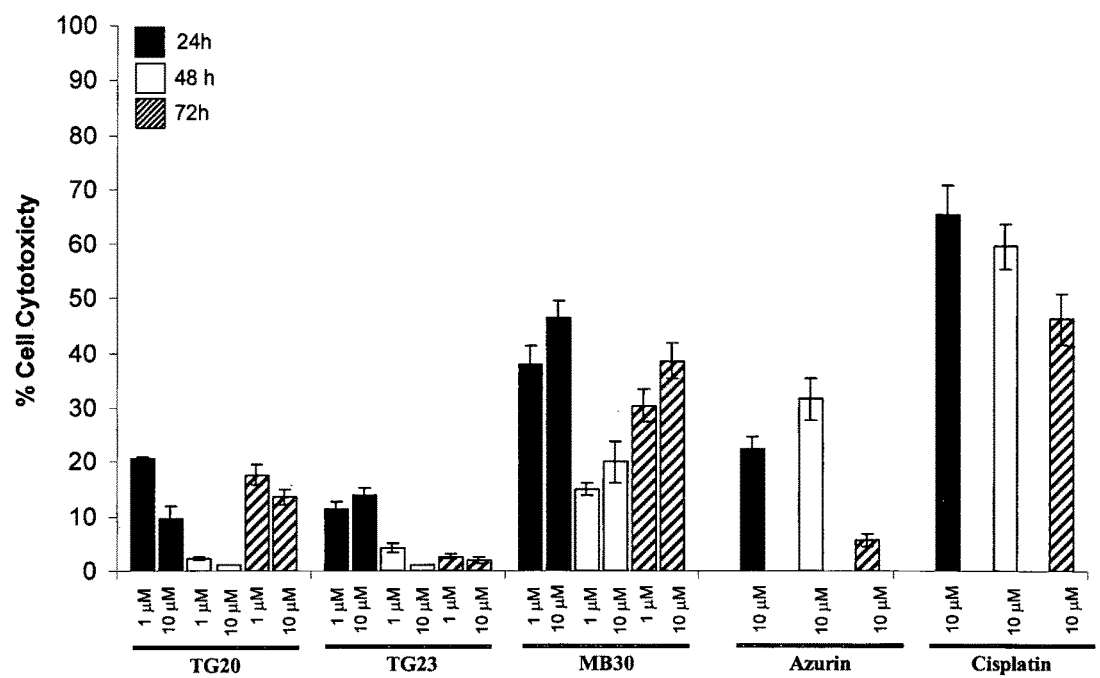
FIG. 1: depicts the cytotoxicity effect of varying concentrations of peptides on HTB-9 bladder cancer cell line, which was comparable with the controls cisplatin and azurin. $1 \times 10^4$ cancer cells were seeded and after 24 h, media were changed with varying concentrations of anticancer peptides (TG20, TG23, and MB30), azurin and cisplatin as positive controls. The viability of the cells was estimated by using MTT assay on the basis of formazan formed, which was detected spectrophotometrically by optical density at 570 nm at 24 h, 48 h and 72 h [Bar-mean±S.E.]

The present invention relates to an anticancer agent with enhanced activity and reduced toxicity, which is a protein of microbial origin having SEQ ID NO. 1 and/or SEQ ID NO. 2 and variants thereof.

The anticancer agent of SEQ ID NO. 1 may be a secreted protein of Mycobacterium tuberculosis, and/or Mycobacterium bovis BCG and termed as MPT 63.

The anticancer agent of SEQ ID NO. 2 may be a surface protein from the parasite Toxoplasma gondii, and termed as SAG1.

The variants of SEQ ID NO. 1 are peptides such as MB30 of SEQ ID NO. 3 and other peptides from other regions having 10 to 50% variation in the amino acid sequence without affecting the anticancer activity.

The variants of SEQ ID NO. 2 are peptides such as TG20 of SEQ ID NO. 4 and TG23 of SEQ ID NO. 5 and other peptides from other regions having 10 to 50% variation in the amino acid sequence without affecting the anticancer activity.

The anticancer agent of the present invention exhibits anticancer activity against the group consisting of melanoma, leukemia, breast, ovarian, cervical, lung, pancreatic, colon, bladder, prostate, liver, renal and brain cancers.

The invention also relates to a pharmaceutical composition comprising an anticancer agent as herein before described.

The pharmaceutical composition may further comprises adjuvant(s).

The anticancer agent may be modified by PEGylation, acetylation, phosphorylation or prepared synthetically. The modification thus made extends the half life of the active ingredient and/or reduce immunogenecity in the blood stream of the subject.

The pharmaceutical composition may be useful for intravenous (iv), intramuscular, oral, subcutaneous or topical application, in presence or absence of adjuvants or excipients for the therapeutic and/or prophylactic treatment of melanoma, leukemia, breast, ovarian, cervical, lung, pancreatic, colon, bladder, prostate, liver, renal and brain cancers.

The applicant has found out that the secreted protein MPT63 and of a peptide, termed MB30, derived from it possess anticancer activity and can be used for treating cancers in mammals. Similarly, they also found out the anticancer activity of a surface protein from the parasite *Toxoplasma gondii*, termed SAG1, and two peptides TG20 and TG23 derived from it. Such proteins and peptides proved to be an excellent candidate drugs to treat a variety of human cancers. The present invention thus provides microbial products as anticancer agents and pharmaceutical compositions comprising isolated and purified proteins or synthetic peptides, and methods of using them for the treatment of cancer. It is very important to develop new anticancer bioactive peptides having high activity and low toxicity; given that most currently available anticancer therapies either have significant toxicity, and/or are prone to development of resistance.

The inventors carrying out research over long period could demonstrate that the *Mycobacterium*-specific secreted protein, MPT63, of hitherto unknown function produced by both the human pathogen *M. tuberculosis* and the bovine strain *M. bovis* and a peptide derived from it termed MB30, exhibit its use in bladder and other cancer therapy.

MPT63 is a small (16 kDa) protein which is secreted after 2-3 weeks of culturing and decreases with longer cultivation. This protein has been shown to have immunogenic property and has been implicated in virulence. It is specific to mycobacteria as homologues of MPT63 have only been found in mycobacterial species like *M. smegmatis, M. bovis* and *M. avium*. A pseudogene of MPT63 has been found within the *M. lapre* genome, but is thought not to be translated into protein. The analysis of DNA sequence encoding MPT63 revealed an ORF encoding a protein of 159 amino acids (aa). It consists of a 130 aa mature protein preceded by 29 aa signal peptide. The X-ray crystal structure of MPT63 was determined to 1.5-Angstrom resolution with the hope of yielding functional information about MPT63. The structure of MPT63 is a β-sandwich consisting of two antiparallel β-sheets similar to an immunoglobulin like fold, with an additional small, antiparallel β-sheet. Apart from immunoglobulin structure, MPT63 has some structural homology to cell surface binding proteins such as Homo sapiens β-adaptin, bovine arrestin and *Yersinia pseudotuberculosis* invasin. It has also structural similarity to eukaryotic fibronectin-binding proteins, major histocompatiblity domains and T-cell receptors. The function of MPT63 has hitherto been unknown and could not be predicted by its structural features as it has an extremely common immunoglobulin like fold that occurs in about 24% of the structures in the Protein Data Bank. The β-sandwich fold that MPT63 resembles is at the core of many proteins with diverse functions.

Interestingly, the inventor also found out that not only pathogenic bacteria and viruses have been shown to allow cancer regression, but a few parasites have also been implicated in this process. For example, concurrent infection by enteric helminth, a parasite, and *Helicobacter felis* in mice can attenuate gastric atrophy, a pre-malignant lesion in mice. The helminth pre-infection was shown to reduce *helicobacter* gastritis but not *H. felis* colonization, presumably due to a shift in the balance of Th1 to Th2 response. However, the production of anticancer agent(s) by the helminths, just as secretion of azurin by *P. aeruginosa* or MPT63 by *M. bovis*, cannot be ruled out.

An interesting case of tumor regression by a parasite is the regression of B16 melanoma cells in mice by *Toxoplasma gondii*, an obligate intracellular parasite that is the causative agent of toxoplasmosis. In absence of *T. gondii* infection, challenge with B16 melanoma cells in mice led to tumor formation. In *T. gondii*-infected mice, however, B16 cells failed to form subcutaneous tumors. To determine if the immune system activation in *T. gondii*-infected mice was responsible for the failure of the B16 melanoma cells to form tumors, a variety of mutant mice lacking major immune functions such as iNOS or perforin where cytolytic functions of lymphocytes were severely reduced, were used. These investigators also used scid-beige mice in which cytotoxic T lymphocytes are absent and NK cells are not cytotoxic. Even in scid-beige and perforin knock-out mice where cytolytic functions of lymphocytes are severely impaired and immune functions are greatly reduced, the anticancer activity of *T. gondii* was clearly evident, suggesting the presence of active anticancer agents produced by *T. gondii*. Further experimentations with blood vessel formation demonstrated that hemoglobin levels in Matrigels from *T. gondii*-infected mice were 50 to 100 fold lower than the control mice without *T. gondii* infection with very little histopathologically-observed vascular channels. This suggested that *T. gondii* infection led to systemic suppression of angiogenesis, although the nature or the origin of the anti-angiogenic agent(s) could not be determined. There was some evidence that the circulating anti-angiogenic factors were soluble and not cell-associated but whether such factors were produced by the mice cells or *T. gondii* could not be determined.

The applicant also demonstrated that the anticancer activity of *T. gondii* can be attributed, at least in part, to the presence of the surface antigen called SAG1. SAG1 is one of the more prominent surface proteins in *T. gondii* involved in host cell attachment and is considered a key virulence factor for *T. gondii*. SAG1 is a 30 kDa immunodominant surface antigenic glycoprotein, also known as P30, highly conserved in *T. gondii* strains, particularly in tachyzoites. The monomelic SAG1 has two domains, a N-terminal 130 amino acid domain D1 and a C-terminal 120 amino acid domain D2. Remarkably, SAG1 shows structural similarity to azurin and interacts with azurin, but it interacts much more strongly with the azurin-like protein Laz. Because SAG1 is surface-associated similar to Laz, and shows structural similarity with the anticancer agents azurin and Laz, it was of great interest to the applicant to determine if similar to Laz, SAG1 might possess anticancer activity against some of the human cancers. To eliminate the likely toxicity of the protein itself in human patients, two peptides TG20 and TG 23, were designed taking advantage of the structural similarities between azurin (and the azurin-like protein Laz) and SAG1. These two peptides were though to harbor the potential anticancer activity of SAG1, somewhat similar to azurin peptides P28 and P26 with known anticancer activity.

Further, TG20 and TG23, derived from different parts of SAG1, did demonstrate anticancer activity against bladder and colon cancers. For comparison purposes, the applicant has also included azurin and cisplatin in assays.

Materials and Methods:

The complete amino acid sequence of MPT63 protein (SEQ ID NO. 1) from *Mycobacterium bovis* is given below. The first 29 amino acids (underlined) in the following MPT63 sequence form secretion signal peptide (leader) sequence and the MB30 peptide (amino acids 44-73 of mature protein) sequence is highlighted in bold.

MKLTTMIKTAVAVVAMAAIATFAEPVALAAYPITGKLGSELTMTDTVGQ

VVLGWKVSDLKSSTAVIPGYPVAGQVWEATATVNAIRGSVTPAVSQFN

ARTADGINYRVLWQAAGPDTISGATIPQGEQSTGKIYFDVTGPSPTIVA

MNNGMQDLLIWEP

The peptide sequence of 30 amino acids derived from MPT63 protein, called MB30, peptide is given below.

MB30 peptide sequence (SEQ ID NO.3):

GQVWEATATVNAIRGSVTPAVSQFNARTAD

The complete amino acid sequence of SAG1 protein (SEQ ID NO. 2) from *Toxoplasma gondii* is given below.

MFPKAVRRAVTAGVFAAPTLMSFLRCGVMASDPPLVANQVVTCPDKKST

AAVILTPTENHFTLKCPKTALTEPPTLAYSPNRQICSAGTTSSCTSKAV

TLSSLIPEAEDSWWTGDSASLDTAGIKLTVPIEKFPVTTQTFVVGCIKG

DDAQSCMVTVTVQARASSVVNNVARCSYGANSTLGPVKLSAEGPTTMTL

VCGKDGVKVPQDNNQYCSGTTLTGCNEKSFKDILPKLTENPWQGNASSD

KGATLTIKKEAFPAESKSVIIGCTGGSPEKHHCTVKLEFAGAAGPAKSA

AGTASHVSIFAMVIGLIGSFAACVA

The peptide sequence of 20 amino acids derived from SAG1 protein of *T. gondii*, termed TG20, is given below.

NHFTLKCPKTALTEPPTLAY

TG20 peptide sequence (SEQ ID NO. 4):

The peptide sequence of 23 amino acids derived from SAG1 protein *T. gondii*, termed TG23, is given below.

TG23 peptide sequence (SEQ ID NO. 5):

TAGIKLTVPIEKFPVTTQTFVVG

For illustrating the invention, experiments detailing the anticancer activity of the bioactive peptides are described below. It should be noted that the following examples are intended to describe such activities and not to limit the invention. The isolation and purification of the proteins have previously been described in the literature while all the peptides were chemically synthesized by commercial concerns. We have cloned and expressed the MPT-63 protein and its anticancer activity was evaluated in various cancer cell lines.

Cloning and Expression of MPT63 Protein:

The MPT63 gene was amplified by PCR using the following primers with NdeI restriction site on the forward primer and HindIII restriction site on the reverse primer:

Forward primer:
5'-TCGATCCATATGGCCTATCCCATCACCGGA-3',
and

Reverse primer:
5'-TCGATCAAGCTTCTACGGCTCCCAAATCAG-3'.

The NdeI and HindIII PCR product is ligated in the pUC18 cloning vector. The MPT63 gene is excised from pUC18 and ligated into prerestricted pET28a expression vector and transformed into *E. coli* BL21de3. For MPT63 purification, a single colony of BL21de3 was inoculated into LB broth and inoculated at 37° C. until the OD reached to 0.5. The culture was induced with 1mM IPTG for overnight at 37° C.

After overnight incubation period, the culture was centrifuged and the cell pellets were incubated on ice for 15 minutes. Cells were re-suspended in 10 ml native lysis buffer with benzonase and lysozyme, incubated on ice for 30 minutes, and intermittently mixed so as to ensure homogenous suspension. Cell lysate was centrifuged at 14000 g/4° C. for 30 minutes to pellet the cellular debris. The cell lysate supernatant was loaded on the Ni-NTA column supplied by Qiagen, and the flow-through fraction was collected. The column was washed twice with wash buffer. The bound 6×His-tagged protein was eluted with two 1 ml aliquots of native elution buffer. Both the elution fractions were collected in separate tubes. At each step of the process, samples were analyzed by SDS PAGE. This purified protein was used in the further experiments at concentration of 1 µM, 5 µM and 10 µM to determine its cytotoxic effect on the various cell lines.

Cell Culture:

Bladder cancer cell lines HTB-9 [Grade II Bladder carcinoma], CRL-1749 (UM-UC-3) [High grade bladder carcinoma], and colorectal carcinoma cell lines CCL-222 (COLO 205) [Dukes Type D colorectal adenocarcinoma], CCL-247 (HCT-116), SiHa, CaSki, MDA-MB-231, U87 and HepG2 were procured from American Type Culture Collection (ATCC). All cell lines were grown under standard conditions in humidified 37° C. incubator in 5% $CO_2$ as described earlier (Garg et al., 2009; Kanojia et al., 2010).

ATCC: HTB-9: Human cell line with epithelial-like characteristics established from a urinary bladder carcinoma (grade II) of a 68 year old male patient. This cell line is tumorigenic in nature. These cells lack a functional retinoblastoma protein, Rb. HTB-9 cells proliferate in response to a variety of growth factors, including IL2, IL3, G-CSF, GM-CSF, and M-CSF. Goselink et al (1996) have shown that the serum-free conditioned medium of HTB-9 cells can replace serum to support the growth of hematopoietic progenitor cells (HPC) in semi-solid cultures.

ATCC: UM-UC-3: Human cell line with epithelial-like characteristics established from a high grade invasive urinary bladder carcinoma of a male patient. This is a hyper-triploid human cell line and IFN non responsive. This cell line is tumorigenic in nature.

ATCC COLO 205: Human cell line derived from colorectal adenocarcinoma Dukes' type D of 70 year old male patient. The cells are CSAP negative. The cells are positive for keratin by immunoperoxidase staining. COLO 205 cells express a 36000 Dalton cell surface glycoprotein related to GA733-2 tumor associated antigen.

ATCC HCT 116: Human cell line with epithelial-like characteristics established from colorectal carcinoma from an adult male patient. The cells are positive for keratin by immunoperoxidase staining. HCT 116 cells are positive for transforming growth factor beta 1 (TGF beta 1) and beta 2 (TGF beta 2) expression. This line has a mutation in codon 13 of the ras protooncogene, and can be used as a positive control for PCR assays of mutation in this codon.

ATCC: SiHa: Human cell line established from fragments of a primary tissue sample obtained after surgery from a Japanese patient. Electron microscopic observations revealed presence of typical desmosomes at the cell junctions and an abundance of tonofilaments in the cytoplasm. The line is reported to contain an integrated human papillomavirus type 16 genome (HPV-16, 1 to 2 copies per cell).

ATCC: CaSki: Human cell line derived from 40 year-old Caucasian female patient. The line was established from cells from a metastasis in the small bowel mesentery. The cells are reported to contain an integrated human papillomavirus type 16 genome (HPV-16, about 600 copies per cell) as well as sequences related to HPV-18.

ATCC: MDA-MB-231: It is a human cell line with epithelial like characteristics established from mammary gland (breast) adenocarcinoma from a 51 year old Caucasian female patient. The cells express the WNT7B oncogene.

ATCC: U87: It is a human glioblastoma cell line formally known as U-87 MG. It has epithelial morphology, and was obtained from 44 year old Caucasian female. patient.

ATCC: HepG2: Human cell line derived from the liver tissue of a 15 year old Caucasian American male with a well differentiated hepatocellular carcinoma. These cells are epithelial in morphology and are not tumorigenic in nude mice. The cells secrete a variety of major plasma proteins; e.g., albumin, transferrin and the acute phase proteins fibrinogen, alpha 2-macroglobulin, alpha 1-antitrypsin, transferrin and plasminogen.

Cytotoxicity Assay:

The cytotoxicity assays performed in this investigation were designed to evaluate the cytotoxic potential of bioactive peptides from Table 1 in cancer cell lines at the given concentrations. MTT [3-(4, 5-dimethylthiazol-2-yl)-2,5-diphenyl tetrazolium bromide] assay was carried out for measurement of the cytotoxicity of different anticancer peptides. The water soluble tetrazolium salt, MTT [3-(4,5-dimethylthiazol-2-yl)-2,5-diphenyl tetrazolium bromide] is metabolized to the water insoluble formazan by intact mitochondrial dehydrogenases. The formazan is then solubilized by adding 2-propanol+40 mM HCl for 4 h incubation. $1\times10^4$ cells were seeded and after 24 h, media were changed with varying concentrations of anticancer peptides (TG20, TG23 and MB30), azurin (known to have anticancer activity, Chakrabarty, 2010) and cisplatin, also a known anticancer compound (Sedletska et al., 2005), as positive controls [Table 1]. The viability of the cells was estimated on the basis of formazan formed, which was detected spectrophotometrically by optical density at 570 nm at 24 h, 48 h and 72 h. At every time point such as 24 h, 48 h and 72 h, $1\times10^4$ cells were seeded without the peptide in triplicate in each plate for a given treatment of peptide. This was used as control cytotoxicity levels to calculate the percent cell cytotoxicity of every peptide treatment. The cytotoxicity of full length protein MPT-63 was also determined using this assay, where protein was used instead of peptides. All the experiments were carried out in triplicates and repeated three times.

TABLE 1

| Peptide TG20 | 1 µM | 10 µM |
| Peptide TG23 | 1 µM | 10 µM |
| Peptide MB30 | 1 µM | 10 µM |
| Azurin | | 10 µM |
| Cisplatin | | 10 µM |

Results:

Treatment with various peptides in this investigation revealed anticancer properties of the peptides. In vitro analysis of cytotoxicity results distinctly revealed reduction in cellular proliferation. All the experiments were carried out in triplicates and repeated three times.

MTT assays demonstrated the cytotoxic activity in HTB-9 bladder cancer cells of all the 3 peptides (TG20, TG23, and MB30, Table 1) when used at concentrations of 1.0 and 10.0 micromolar, along with the other positive controls azurin and cisplatin. All the three peptides demonstrated cytotoxicity up to 40% and 60% at 48 and 72 h respectively, comparable to azurin and cisplatin (FIG. 1). Such results demonstrated that peptide concentrations as low as 1.0 micromolar were enough and higher concentrations did not add substantially to the cytotoxicity. Also, while low at 24 h, the cytotoxicity levels increased with increasing times of incubation up to 72 h (FIG. 1).

Figure 2:
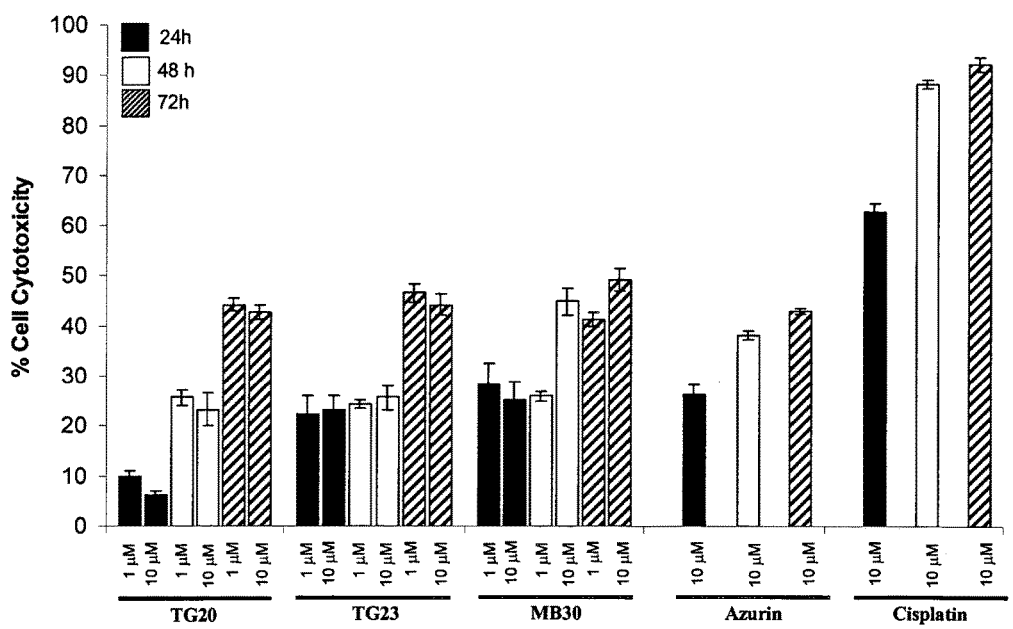
FIG. 2: Depicts the cytotoxicity effect of varying concentrations of peptides on UM-UC-3 bladder cancer cell line, which was comparable with the controls cisplatin and azurin. $1 \times 10^4$ cancer cells were seeded and after 24 h, media were changed with varying concentrations of anticancer peptides (TG20, TG23, and MB30), azurin and cisplatin as positive controls. The viability of the cells was estimated by using MTT assay on the basis of formazan formed, which was detected spectrophotometrically by optical density at 570 nm at 24 h, 48 h and 72 h [Bar-mean+S.E.].

In order to assess the cytotoxicity of all these peptides in different bladder cancer cell lines, UM-UC-3 bladder carcinoma cell line was incubated with the peptides at 1.0 and 10 µM concentrations and cytotoxicity was monitored at 24, 48 and 72 hours. At 24 h, TG23 and MB30 peptides demonstrated higher cytotoxicity levels than the other peptide, comparable to azurin but less than cisplatin. With prolonged exposure up to 72 h, all the three peptides demonstrated about 45% cytotoxicity in the UM-UC-3 bladder cancer cell line (FIG. 2).

Figure 3:
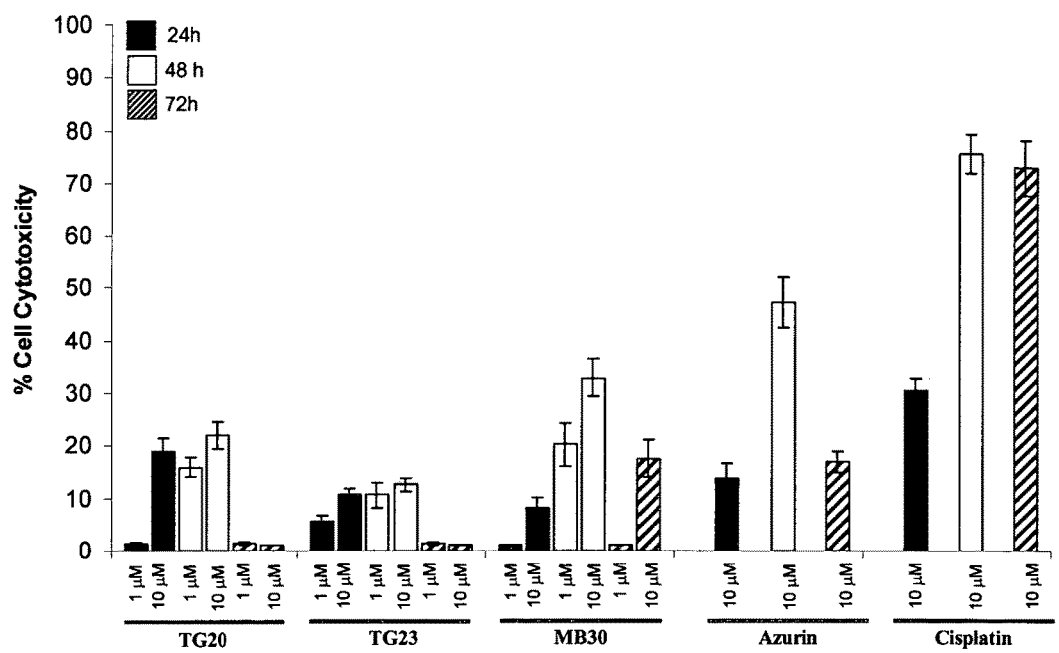
FIG. 3: Depicts the cytotoxicity effect of varying concentrations of peptides on COLO 205 colorectal cancer cell line, which was comparable with the controls cisplatin and azurin. $1 \times 10^4$ cancer cells were seeded and after 24 h, media were changed with varying concentrations of anticancer peptides (TG20, TG23 and MB30), azurin and cisplatin as positive controls. The viability of the cells was estimated by using MTT assay on the basis of formazan formed, which was detected spectrophotometrically by optical density at 570 nm at 24 h, 48 h and 72 h [Bar-mean+S.E.]

Although the ability of live cells of M. bovis BCG to allow regression of cancers such as melanoma, prostate or leukemia has been reported in the past, such effects were not consistent. The consistent efficacy in human patients was only against bladder cancer. To evaluate if the MB30 peptide or the other peptides would demonstrate cytotoxicity against other cancers, the cytotoxicity of all the three peptides was also assessed in a colon cancer cell line, called COLO 205, at various concentrations up to 72 hour. All the three peptides demonstrated varying cytotoxicity, about 10-20%, during 48 h incubation (FIG. 3).

Figure 4:
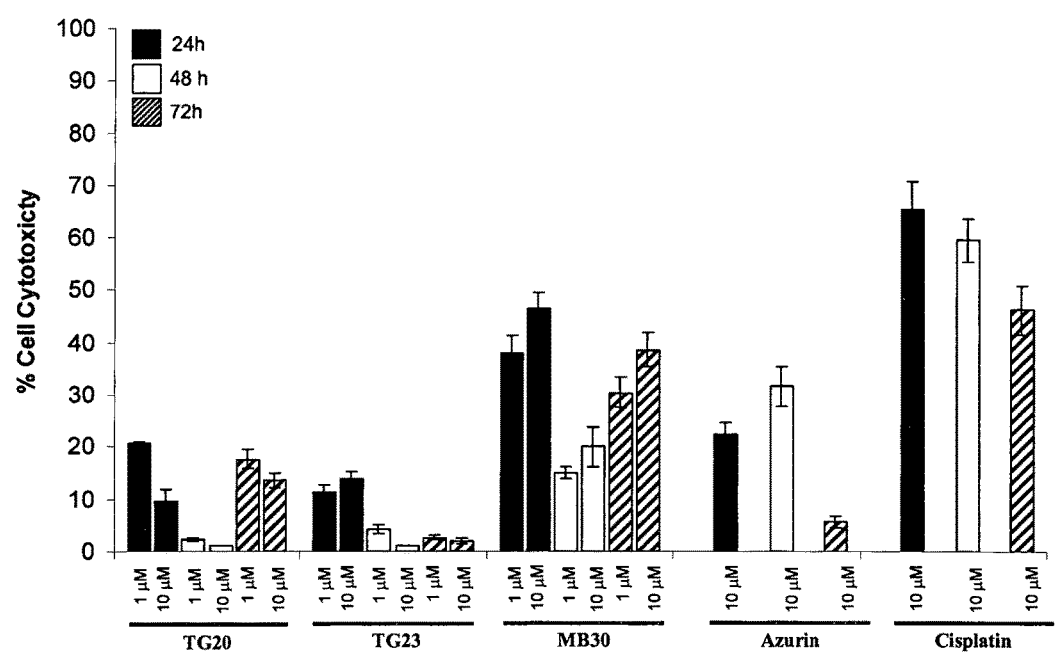
FIG. 4: Depicts the cytotoxicity effect of varying concentrations of peptides on HCT 116 colorectal cancer cell line, which was comparable with the controls cisplatin and azurin. $1 \times 10^4$ cancer cells were seeded and after 24 h, media were changed with varying concentrations of anticancer peptides (TG20, TG23 and MB30), azurin and cisplatin as positive controls. The viability of the cells was estimated by using MTT assay on the basis of formazan formed, which was detected spectrophotometrically by optical density at 570 nm at 24 h, 48 h and 72 h [Bar-mean+S.E.].
Figure 5:
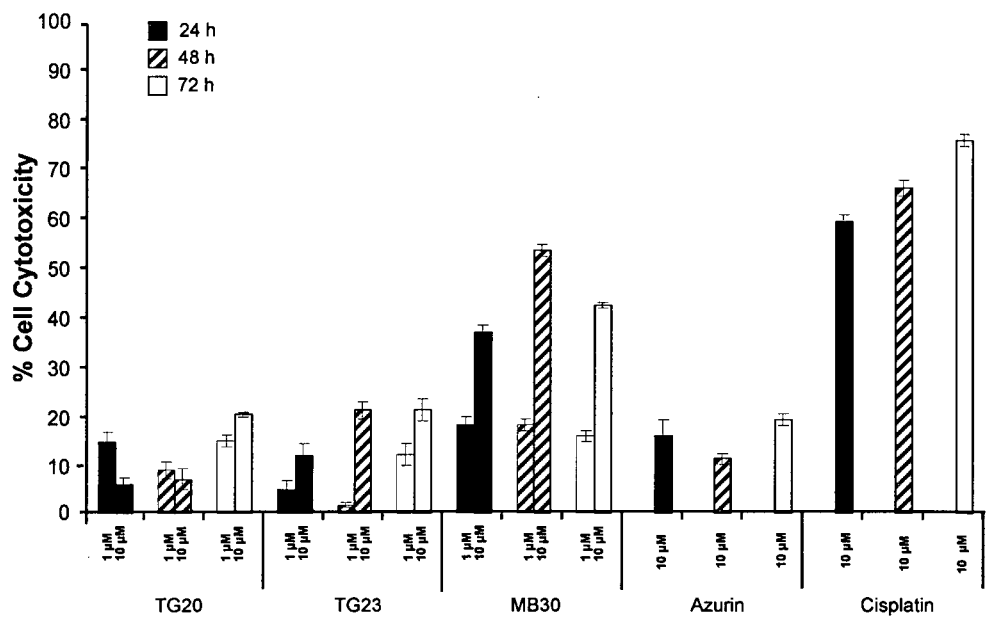
FIG. 5: Depicts the cytotoxicity effect of varying concentrations of peptides on SiHa cervix cancer cell line which was comparable with the controls cisplatin and azurin. $1 \times 10^4$ cancer cells were seeded and after 24 h, media were changed with varying concentrations of anticancer peptides (TG20, TG23 and MB30), azurin and cisplatin as positive controls. The viability of the cells was estimated by using MTT assay on the basis of formazan formed, which was detected spectrophotometrically by optical density at 570 nm at 24 h, 48 h and 72 h [Bar-mean±S.E.].
Figure 6:
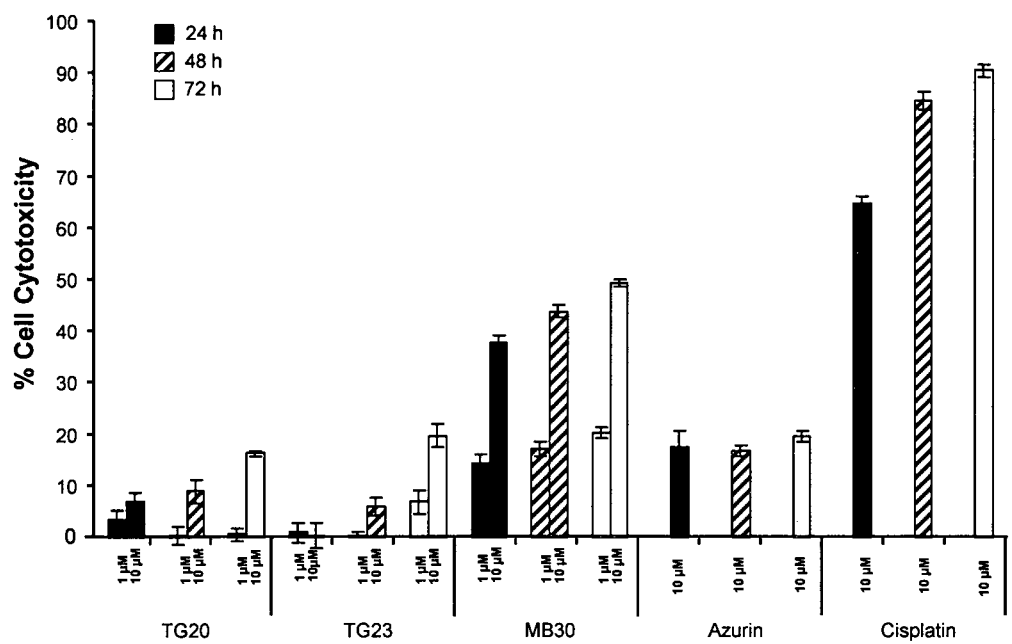
FIG. 6: Depicts the cytotoxicity effect of varying concentrations of peptides on CaSki cervix cancer cell line which was comparable with the controls cisplatin and azurin. $1 \times 10^4$ cancer cells were seeded and after 24 h, media were changed with varying concentrations of anticancer peptides (TG20, TG23 and MB30), azurin and cisplatin as positive controls. The viability of the cells was estimated by using MTT assay on the basis of formazan formed, which was detected spectrophotometrically by optical density at 570 nm at 24 h, 48 h and 72 h [Bar-mean±S.E.].
Figure 7:
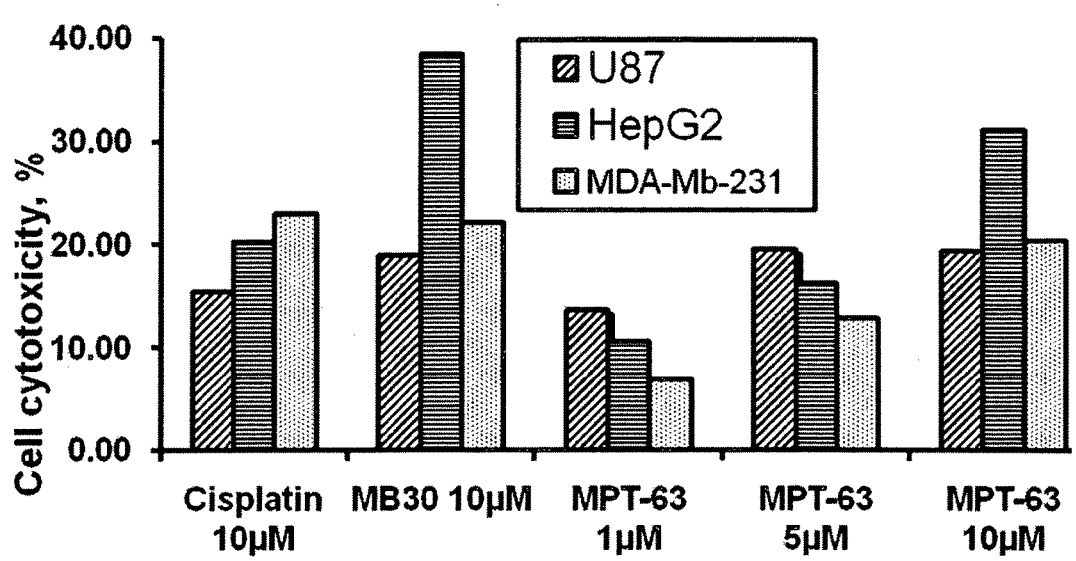
FIG. 7: Depicts the cytotoxicity effect of MB30 peptide and MPT-63 protein on U87 human glioblastoma, HepG2 liver cancer and MDA-MB-231 breast cancer cell lines. $1 \times 10^4$ cancer cells were seeded and after 24 hours it was treated separately with varying concentrations of either MB30 peptide or MPT63 protein or cisplatin as a positive control. The viability of the cells were estimated by using MTT assay on the basis of formazan formed, which was detected spectrophotometrically by measuring optical density at 570 nm at 24 h and % cell cytotoxicity was determined.

The anticancer activity of all the three peptides was also checked in the colon cancer cell line HCT 116 and in cervical cancer cell lines (SiHa and CaSki). The peptide MB30 killed about 40% of the colon and cervical cancer cells at both the concentrations when incubated up to 24 h, higher than azurin but somewhat less than cisplatin. The other peptides TG20 and TG23 showed less cytotoxicity (FIGS. 4, 5 and 6). Such data clearly indicate that peptides like MB30, as well as TG20 and TG23, demonstrate significant cytotoxicity in bladder and other cancer cells. The full length MPT-63 protein was purified and its cytotoxicity was compared with MB30 peptide in U87, HepG2 and MDA-MB-231 cell lines. The MPT-63 protein has also shown cytotoxicity in all the three cell lines (brain, liver and breast cancers) tested (FIG. 7). However, the MB30 peptide has demonstrated better cytotoxicity in comparison to the full length protein MPT-63 in all the three cell lines (brain, liver and breast cancers) at 24 h (FIG. 7). This indicates that the full length protein as well as MB30 peptide shows anticancer activities in a variety of cancer cell lines.

REFERENCES

1. Basturk, B., Yavascaoglu, I., Oral, B., Goral, G. and Oktay, B. 2006. Cytokine gene polymorphisms can alter the effect of *Bacillus* Calmette-Guerin (BCG) immunotherapy. Cytokine 35:1-5.
2. Bisiaux, A., Thiounn, N., Timsit, M. O., Eladaui, A., Chang, H. H. et al. 2009. Molecular analyte profiling of the early events and tissue conditioning following intravesical *bacillus* Calmette_Guerin therapy in patients with superficial bladder cancer. J. Urol. 181:1571-1580.
3. Bohle, A., Jocham, D. and Bock, P. R. 2003. Intravesical *bacillus* Calmette-Guerin versus mitomycin C for superficial bladder cancer: A formal meta-analysis of comparative studies on recurrence and toxicity. J. Urol. 169:90-95.
4. Chakrabarty, A. M. 2010. Bioengineered bugs, drugs and contentious issues in patenting. Bioengineered Bugs 1:2-8.
5. Chaudhari, A., Mahfouz, M., Fialho, A. M., Yamada, T., Granja, A. T., Zhu, Y., Hashimoto, W., Schlarb-Ridley, B., Cho, W., Das Gupta, T. K. and Chakrabarty, A. M. 2007. Cupredoxin-cancer interrelationship: Azurin binding with EphB2, interference in EphB2 tyrosine phosphorylation, and inhibition of cancer growth. Biochemistry 46:1799-1810.
6. Decobert, M., Larue, H., Bergeron, A., Harel, F., Pfister, C, Rousseau, F., Lacombe, L. and Fradet, Y. 2006. Polymorphisms of the human NRAMP1 gene are associated with response to *bacillus* Calmette-Guerin immunotherapy for superficial bladder cancer. J. Urol. 175:1506-1511.
7. Fialho, A. M. and Chakrabarty, A. M. 2010a. Emerging Cancer Therapy: Microbial Approaches and Biotechnological Tools. John Wiley & Sons, Inc., New York.
8. Fialho, A. M. and Chakrabarty, A. M. 2010b. Promiscuous anticancer drugs from pathogenic bacteria: Rational versus intelligent drug design. In Emerging Cancer Therapy: Microbial Approaches and Biotechnological Tools, A. M. Fialho and A. M. Chakrabarty, Eds., pages 181-198, John Wiley & Sons Inc., New York.
9. Garg, M., Kanojia, D., Seth, A., Kumar, R., Gupta, A., Surolia, A., and Suri, A. 2009. Heat-Shock Protein 70-2 (HSP70-2) Expression in Bladder Urothelial Carcinoma is Associated with Tumor Progression and Promotes Migration and Invasion. Eur J Cancer. 46:207-215.
10. Goselink, H. M., van Damme, J., Hiemstra, P. S., Wuyts, A., Stolk, J., Fibbe, W. E., Willemze, R., Falkenburg, J. H. 1996. Colony growth of human hematopoietic progenitor cells in the absence of serum is supported by a proteinase inhibitor identified as antileukoproteinase. J Exp Med. 184:1305-1312.
11. Herr, H. W. and Morales, A. 2008. History of *bacillus* Calmette-Guerin and bladder cancer: an immunotherapy success story. J. Urol. 179:53-56.
12. Hong, C. S., Yamada, T., Hashimoto, W., Fialho, A. M., Das Gupta, T. K. and Chakrabarty, A. M. 2006. Disrupting the entry barrier and attacking brain tumors: The role of the *Neisseria* H.8 epitope and the Laz protein. Cell Cycle 5:1633-1641.
13. Jemal, A., Siegel, R., Ward, E., Hao, Y., Xu, J., Murray, T., Thun, M. J. and Ward E. 2008. Cancer statistics. C A Cancer J. Clin. 58:71-96.
14. Kanojia, D., Garg, M., Gupta, S., Gupta, A., and Suri, A. 2010. Sperm-Associated Antigen 9 Is a Novel Biomarker for Colorectal Cancer and Is Involved in Tumor Growth and Tumorigenicity. Am J Pathol. 178:1009-1020.
15. Kresowik, T. P. and Griffith, T. S. 2010. *Bacillus* Calmette-Guerin (BCG) for urothelial carcinoma of the bladder. In Emerging Cancer Therapy: Microbial Approaches and Biotechnological Tools, A. M. Fialho and A. M. Chakrabarty, Eds., pages 49-70, John Wiley & Sons Inc., New York.
16. Ludwig, A. T., Moore, J. M., Luo, Y., Chen, X., Saltsgaver, N. A., O'Donnell, M. A. and Griffith, T. S. 2004. Tumor-necrosis factor-related apoptosis-inducing ligand: A novel mechanism for *Bacillus* Calmette-Guerin-induced antitumor activity. Cancer Res. 64:3386-3390.
17. Mahfouz, M., Hashimoto, W., Das Gupta, T. K. and Chakrabarty, A. M. 2007. Bacterial proteins and CpG-rich extrachromosomal DNA in potential cancer therapy. Plasmid 57:4-17.
18. Richards, J M., Warso, M A., Mehta, D., Christov, K., Schaeffer, C M., Yamada, T., Beattie, C W., Bressler, L R and Das Gupta, T K. 2011. A first-in-class, first-in-human phase I trial of p28, a non-HDM2-mediated peptide inhibitor of p53 ubiquitination in patients with metastatic refractory solid tumors. J. Clin. Oncol. 29:2511.
19. Sedletska, Y., Giraud-Panis, M. J. and Malinge, J. M. 2005. Cisplatin is a DNA-damaging antitumour compound triggering multifactorial biochemical responses in cancer cells: Importance of apoptotic pathways. Curr. Med. Chem. Anticancer Agents 5: 251-265.
20. Shintani, Y., Sawada, Y., Inagaki, T., Kohjimoto, Y., Uekado, Y. and Shinka, T. 2007. Intravesical instillation therapy with *bacillus* Calmette-Guerin for superficial bladder cancer: Study of the mechanism of *bacillus* Calmette-Guerin immunotherapy. Intl. J. Urol. 14:140-146.
21. Sylvester, R. J., van der Meijden, A. P., Oosterlinck, W., Hoeltl, W. and Bono, A. V. 2003. The side effects of *Bacillus* Calmette-Guerin in the treatment of Ta T1 bladder cancer do not predict its efficacy: Results from a European Organisation for Research and Treatment of Cancer Genito-Urinary Group Phase III trial. Eur. Urol. 44:423-428.
22. Taylor, B. N., Mehta, R. R., Yamada, T., Lekmine, F., Christov, K., Chakrabarty, A. M., Green, A., Bratescu, L., Shilkaitis, A., Beattie, C W. and Das Gupta, T. K. 2009. Noncationic peptides obtained from azurin preferentially enter cancer cells. Cancer Res. 69:537-546.

What is claimed is:

1. A pharmaceutical composition comprising:

(i) an isolated peptide sequence consisting of SEQ ID NO:3 with a modification selected from the group consisting of PEGylation, acetylation, and phosphorylation and (ii) pharmaceutically acceptable adjuvants or excipients.

2. A composition comprising an isolated peptide sequence consisting of SEQ ID NO:3 and a modification selected from the group consisting of PEGylation, acetylation, and phosphorylation.

* * * * *